United States Patent [19]

Campbell et al.

[11] Patent Number: 5,690,912
[45] Date of Patent: Nov. 25, 1997

[54] $SNF_2$ GEL OF IMPROVED STAND-UP AND EFFICACY IN THE TREATMENT OF DENTINE HYPERSENSITIVITY

[75] Inventors: Shannon K. Campbell, North Brunswick; Edward Albert Tavss, Kendall Park, both of N.J.; George Edward Fusiak, Louisville, Ky.; Marilou Joziak, South River; Steven W. Fisher, Middlesex, both of N.J.

[73] Assignee: Colgate Palmolive Company, New York, N.Y.

[21] Appl. No.: 200,034

[22] Filed: Apr. 25, 1994

[51] Int. Cl.⁶ .............................. A61K 7/16; A61K 7/18
[52] U.S. Cl. ...................... 424/52; 424/49; 424/673
[58] Field of Search .................... 424/526.73, 49-58

[56] References Cited

U.S. PATENT DOCUMENTS

| | | | |
|---|---|---|---|
| 3,574,824 | 4/1971 | Echeandia et al. | 424/50 |
| 4,418,057 | 11/1983 | Groat et al. | 424/151 |
| 4,533,544 | 8/1985 | Groat et al. | 424/52 |
| 4,837,008 | 6/1989 | Rudy et al. | 424/53 |
| 4,897,258 | 1/1990 | Rudy et al. | 424/53 |
| 5,023,074 | 6/1991 | Morton et al. | 424/52 |
| 5,071,638 | 12/1991 | Yoshie et al. | 424/49 |

FOREIGN PATENT DOCUMENTS

| | | | |
|---|---|---|---|
| 0075446 | 3/1983 | European Pat. Off. | A61K 7/18 |
| 0162574 | 11/1985 | European Pat. Off. | A61K 7/18 |
| 2216005 | 10/1989 | United Kingdom | A61K 7/16 |

OTHER PUBLICATIONS

Patent Abstracts of Japan vol. 9, No. 205 (C-299) (1928) 22 Aug. 1985 JP A, 60 075 417 (Raion K.K.) 27 Apr. 1985 polyethylene glycol added to provide a dentefrice having improved shape retainability and stability 1% to 8% esp. 2% to 5 % of polyethylene glycol having an average molecular weight of 200 to 600.

*Primary Examiner*—Shep K. Rose
*Attorney, Agent, or Firm*—Paul Shapiro

[57] ABSTRACT

A gel composition exhibiting improved stand-up and efficacy in treating dentine hypersensitivity which composition contains about 0.3 to about 1.0% by weight $SnF_2$, about 87 to about 97% by weight anhydrous glycerine and about 2.0 to about 10% by weight of a polyethylene glycol having an average molecular weight of 1000.

6 Claims, 2 Drawing Sheets

SNF₂ GEL OF IMPROVED STAND-UP AND EFFICACY IN THE TREATMENT OF DENTINE HYPERSENSITIVITY

BACKGROUND OF THE INVENTION

1. Field of the Invention

This invention relates to a dental gel containing stannous fluoride, and more particularly to a stannous fluoride gel having improved stand-up and efficacy in the treatment of dentine hypersensitivity.

2. The Prior Art

Stannous fluoride ($SnF_2$) has been reported to be an effective agent for treating various oral conditions. Included in the dental benefits imparted by $SnF_2$ is the reduction of dental caries. The anticaries benefit has been attributed to the fluoride ion component of the $SnF_2$ salt.

$SnF_2$ has also been indicated clinically to be efficacious in the reduction of dentinal hypersensitivity. This latter therapeutic effect is believed to be attributable, to a large degree, to the stannous ion ($Sn^{2+}$) component of the salt.

Hypersensitive teeth can cause pain and discomfort when subjected to changes in temperature, pressure, or chemical action. Exposure of the dentine, which is generally due to recession of the gums or periodontal surgery, frequently leads to hypersensitivity. The art has determined that dentine tubules open to the surface have a high correlation with dentine hypersensitivity, Absi, J. Clin. Periodontal. 14,280–4(1987). Dentinal tubules lead from the pulp to the surface of the dentine. When the surface of the tooth is eroded, the dentinal tubules become exposed to the external environment. The exposed dentinal tubules provide a pathway for transmission of fluid flow to the pulpal nerves and this is induced by changes in temperature, pressure and ionic gradients. $SnF_2$ is believed to be effective in desensitization of exposed dentinal tubules wherein occlusive deposits of low solubility complexes of tin are formed on the surface of exposed dental tubules effectively blocking the openings. By blocking the tubules, the external stimuli have a diminished effect, and less pain is felt.

In order for $Sn^{2+}$ to be efficacious it must be stable and freely available and not in chemical combination with other ingredients. Stannous fluoride as a 0.4% by weight $SnF_2$ preparation has most frequently been demonstrated to be the concentration of choice in the treatment of dental caries and dentine hypersensitivity.

Due to the chemical instability of stannous fluoride in aqueous solutions, the fluoride salt is normally applied to the teeth as a nonaqueous gel wherein anhydrous glycerine is a carrier for the $SnF_2$ salt. $SnF_2$ in the form of a solution in anhydrous glycerine is presently provided to the professional for use as a topical treatment in the dental office. The professional dilutes this formulation with an aqueous solution immediately prior to application to the teeth.

While topical applications are frequently performed in the dental office there is also a need for follow-up daily application and use by the patient. Thus, "home-care" or "patient-care" availability is desirable. For this purpose a gel with the requisite physical properties to accommodate toothbrush application is the desired marketable form. Unfortunately, $SnF_2$ dissolved in anhydrous glycerine, the form found most suitable for preserving the chemical stability of $SnF_2$, does not lend itself to application with a toothbrush. For example, U.S. Pat. No. 4,418,057 and U.S. Pat. No. 4,533,544 disclose topical preparations of 0.40% $SnF_2$ which are chemically stable when suspended in anhydrous glycerin thickened with hydroxyethylcellulose. A drawback to these gel preparations is that the gels have a semi-liquid consistency, and when dispensed on the bristles of a toothbrush, the gel immediately sinks through the bristles and runs off the brush so that only a relatively small portion of the dispensed product is retained on the toothbrush. Consequently, $SnF_2$ suspended in thickened anhydrous glycerin has not found wide acceptability as a home-care product as the semi-fluid gel composition cannot be controllably retained to the surface of toothbrush bristles and then applied to teeth to reliably supply $SnF_2$ for the treatment of dental caries or dentine hypersensitivity.

Therefore, to preclude the erratic, inconsistent applications of $SnF_2$ encountered with the $SnF_2$ semi-liquid gels of the prior art, there is a need in the art for a $SnF_2$ gel preparation that has improved "stand-up" properties, i.e., the gel has an extrudable consistency such that extruded ribbons of the gel, when dispensed onto the bristles of a toothbrush, will stand-up on the top surface of the bristles for a time sufficient to allow full application to the teeth, e.g., a time interval of at least 0.5–1.0 minute.

SUMMARY Of THE INVENTION

In accordance with the present invention there is provided a chemically and cosmetically (physically) stable, clinically effective dental gel composition which has stand-up properties suitable for toothbrush applications and exhibits an unexpected, improved efficacy in the treatment of dentine hypersensitivity, the composition containing $SnF_2$, anhydrous glycerine and a polyethylene glycol having an average molecular weight of 1000.

Due to the improved stand-up property of the gel $SnF_2$ of the present invention, the gel is readily extrudable onto the bristles of a toothbrush and substantially no sinking of the gel through the bristles is encountered for at least two minutes from the time of extrusion thereon, making the gel product convenient and useful for home use applications. Further, the unexpected improvement in the reduction of dentine hypersensitivity obtained with the gel of the present invention increases the utility of the gel for the treatment of oral conditions.

The present inventive improvement in gel stand-up and efficacy in the treatment of dentine hypersensitivity exhibited by the $SnF_2$ gel of the present invention is predicated on the incorporation in the gel of the specific polyethylene glycol ingredient. As will hereinafter be demonstrated, attempts to prepare $SnF_2$ gels with polyethylene glycols of an average molecular weight substantially less or greater than 1000 result in gels which either have semi-liquid consistencies, are cosmetically unstable, or $SnF_2$ formulations in which the gel structures are not attainable therewith.

DESCRIPTION OF THE PREFERRED EMBODIMENTS

Figure 1:
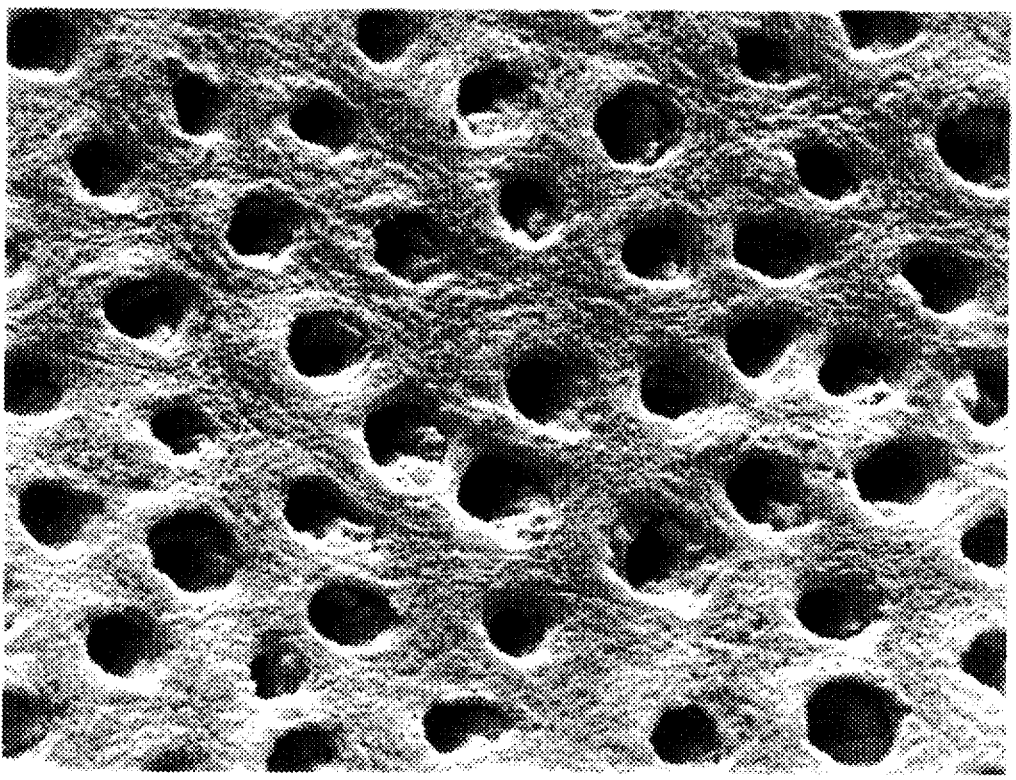
FIG. 1 is a photomicrograph taken at 2500X magnification of the coronal side of a dentine section that had been treated with a placebo dental gel which did not contain $SnF_2$.

The $SnF_2$ gel compositions of the present invention are generally comprised of about 0.30 to about 1.8% by weight $SnF_2$ and preferably about 0.35 to about 0.50% by weight; about 87 to about 97% by weight anhydrous glycerine and preferably about 90 to about 95% by weight and about 2.0 to about 10.0% by weight of polyethylene glycol having an average molecular weight of 1000 and preferably about 5.0 to about 8.0% by weight.

The polyethylene glycol used in the practice of the present invention is a nonionic polymer of ethylene oxide having an average molecular weight of 1000 and the general formula

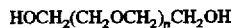

wherein n represents the average number of oxyethylene groups, such polyethylene glycol being designated hereinafter as polyethylene glycol 1000, the number 1000 representing the average molecular weight.

Also included in the compositions of the present invention is an effective flavoring amount of a flavor compatible and stable with the stannous fluoride salt. The flavor ingredient constitutes about 0.05 to about 1% by weight and preferably about 0.1 to about 0.5% by weight of the gel composition. Suitable flavoring constituents are flavoring oils, e.g. oils of spearmint, peppermint, wintergreen, clove, methyl salicylate and menthol.

If desired other agents such as potassium nitrate, stronthium chloride and potassium citrate known to be efficacious in the treatment of hypersensitivity may be included in the compositions of the present invention.

Thickening agents may optionally be included in the $SnF_2$ gels of the present invention at a concentration of about 0.01 to about 0.5% by weight. Suitable thickening agents include hydroxyethyl cellulose and water soluble salts of cellulose ethers such as sodium carboxymethyl cellulose and sodium carboxymethyl hydroxy ethyl cellulose as well as natural gums.

The SnF2 dental gel of this invention may be prepared by suspending $SnF_2$, flavor and polyethylene glycol 1000 in anhydrous glycerine heated to a temperature of 35° to 140° C. by mixing in any suitable mixer, such as a Lightening mixer for about 30 minutes until a homogenous solution is formed. A substantially rigid non-fluid gel product is obtained upon cooling. The final product may be packaged in any suitable container compatible with $SnF_2$ such as plastic or laminate tubes or bottles.

The gel product has an extrudable consistency and upon being extruded as a ribbon onto the bristles of a toothbrush, the ribbon remains in a stand-up position on the toothbrush without substantially sinking through the bristles for at least two minutes.

The following examples are further illustrative of the present invention, but it is understood that the invention is not limited thereto. All amounts and proportions referred to herein and the appended claims are by weight.

EXAMPLE 1

A $SnF_2$ gel of the present invention was prepared with the following ingredients:

| Ingredient | Concentration (wt %) |
|---|---|
| Glycerine | 94.4423 |
| Polyethylene glycol 1000 | 6.00 |
| $SnF_2$ | 0.4000 |
| Flavor (Creme de menthe) | 0.1577 |

The glycerine, flavor and polyethylene glycol 1000 were premixed at 100° C. for 30 minutes to form a homogenous solution. The solution was then mixed with $SnF_2$ for 30 minutes at a speed of 800 revolutions/min with a Lightning mixer. When cool the resultant gel was cosmetically attractive and was tubed in plastic laminate tubes.

The dental gel as prepared above was of extrudable consistency. When a ribbon of the gel was extruded onto the bristles of a toothbrush, the ribbon remained firm and did not sink through the bristles for at least 2 minutes.

For purposes of comparison, the procedure of the example was repeated except polyethylene glycols (PEG) of differing molecular weights (M.W.) other than 1000 were substituted for polyethylene glycol 1000. The ingredients of these comparative dental gels are listed below.

| Comparative Dental Gel | PEG (M.W.) | PEG (Wt %) | Glycerine (Wt %) | $SnF_2$ (Wt %) | HEC* (Wt %) | Flavor (Wt %) |
|---|---|---|---|---|---|---|
| A | 600 | 7 | 92.05 | 0.4 | 0.05 | 0.5 |
| B | 900 | 7 | 92.05 | 0.4 | 0.05 | 0.5 |
| C | 1450 | 7 | 92.09 | 0.4 | 0.01 | 0.5 |
| D | 2000 | 5 | 94.05 | 0.4 | 0.05 | 0.5 |
| E | 4000 | 7 | 91.9 | 0.4 | 0.20 | 0.5 |

*Hydroxyethyl cellulose

Gels structures could not be formed with PEG 600 and PEG 4000 (compositions A and E).

To determine cosmetic (physical) stability, tubed gel formulations of Example 1 as well as comparative gels B–D were exposed to accelerated aging at 120° F. for 1–12 weeks. These aging conditions were found to have good correlation with 2 years storage stability at 20° C. The results of these aging tests are summarized in Table 1 below.

TABLE I

| Dental Gel | PEG | AGING TESTS No. Weeks Aging | Cosmetic Stability After Aging |
|---|---|---|---|
| Ex 1 | 1000 | 12 | No phase separation Good Standup |
| B | 900 | 12 | No phase separation No stand-up |
| D | 1450 | 1 | Phase separation |
| E | 2000 | 1 | Phase separation |

The Aging Test results indicate that only the composition of Example 1 containing polyethylene glycol 1000 exhibited acceptable cosmetic stability wherein no phase separation occurred during the 12 week test period and after this period the dental gel continued to exhibit acceptable stand-up properties.

The chemical stability of the composition of Example 1 was determined by aging the tubed dental gel at 105° F. for 12 weeks. When analyzed for $Sn^{2+}$ content by titration with potassium iodate, the aged gel of Example 1 was determined to have encountered very little $Sn^{2+}$ loss, that is, a loss of 0.01% $Sn^{2+}$, and no $Sn^{2+}$ had reacted with any of the ingredients of the gel.

The gel composition of the present invention was therefore determined to be of excellent cosmetic and chemical stability.

EXAMPLE 2

This gel composition of the present invention was also determined to exhibit improved efficacy against dentinal hypersensitivity.

The efficacy of the gel composition of Example I was demonstrated in accordance with an in vitro procedure found to correlate with clinical efficacy wherein eight hundred micron thick coronal dentine disks were cut from human molars and etched for 2 minutes in 6 percent citric acid to remove the smear layer. The coronal side of each disk was then given multiple 60 second in vitro treatments (3 times daily) for 10 days using a soft toothbrush followed by brief rinsing. Disks were continuously rinsed by fresh, 37° C. phosphate buffer (0.1 mM Ca, 0.06 mM $PC_4$, 0.1M NaCl) between treatments. After treatment, the disks were rinsed well in deionized water and dried. The so treated coronal surfaces were examined by a scanning electron microscope to determine the level of dentine tubule occlusion, the level of occlusion being approximately proportional to the degree of relief from hypersensitivity pain to be expected from the treatment. For purposes of comparison, the treatments included another anhydrous glycerine gel containing 0.4% by weight $SnF_2$.

The comparative $SnF_2$ gel was of the type disclosed in U.S. Pat. Nos. 4,418,057 and U.S. Pat. No. 4,533,544 and had the following composition:

| Ingredient | Wt. % |
| --- | --- |
| Glycerine | 91.7750 |
| $SnF_2$ | 0.4000 |
| HEC | 0.4047 |
| Flavor | 0.1558 |

A placebo identical the Example I composition except that it did not contain $SnF_2$ was also included in the dentine treatments.

Figure 2:
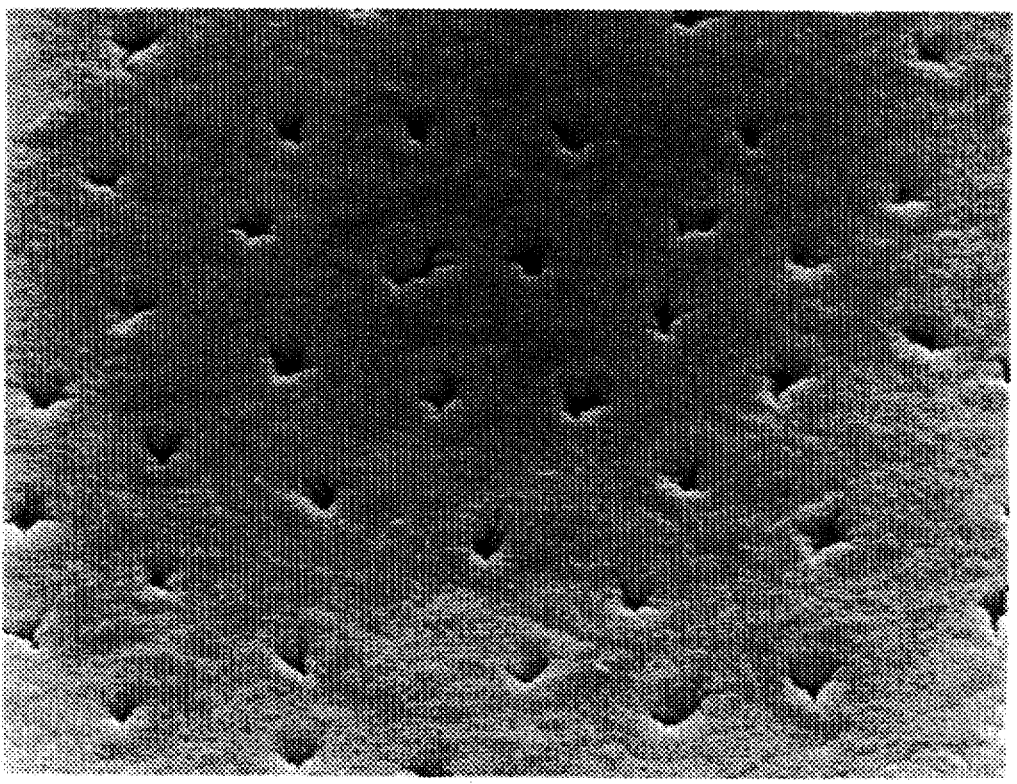
FIG. 2 is an electron photomicrograph taken at 2500X magnification of the coronal side surface of a dentine section that had been treated with a comparative dental gel containing 0.4%, % by weight $SnF_2$.
Figure 3:
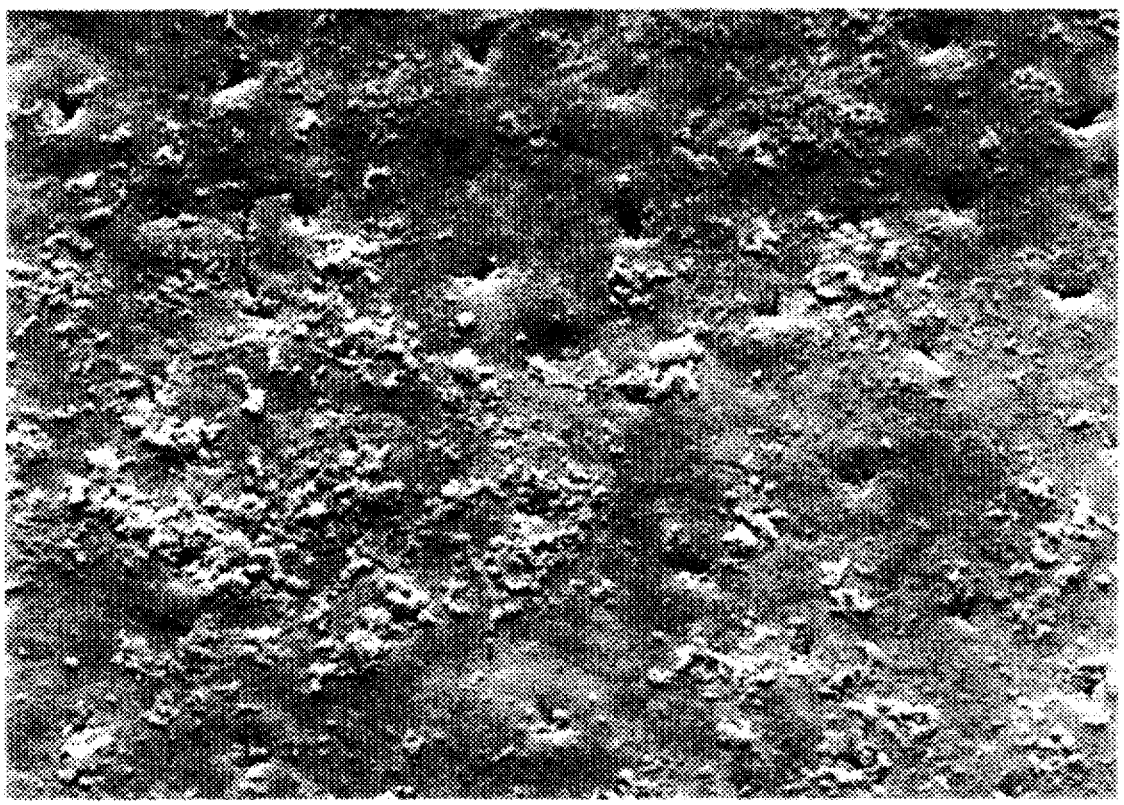
FIG. 3 is a photomicrograph taken at 2500X magnification of the coronal side of a dentine section that had been treated with a dental gel of the present invention containing 0.4% by weight $SnF_2$.

Photomicrographs (2500X) of the treated dentine surfaces were taken and are reproduced in FIGS. 1–3.

FIG. 1 shows the exposed, untilled craters of the dentine tubules after treatment of the dentine with the placebo composition.

FIG. 2 of the dentine after treatment with the comparative 0.4% $SnF_2$ gel which did not contain polyethylene glycol 1000 indicates that only partial occlusion of the dentine tubules occurred.

FIG. 3 of the dentine treated with the gel composition of the present invention shows substantially full occlusion of the tubules, indicating that greater relief from hypersensitivity pain would be expected from the composition of the present invention than from the comparative composition, in spite of the fact that both compositions contained 0.4% by weight $SnF_2$.

What is claimed is:

1. A gel composition exhibiting improved stand-up and efficacy in treating dentine hypersensitivity which composition comprises about 0.3 to about 1.8% by weight $SnF_2$, about 87 to about 97% by weight anhydrous glycerine and about 2.0 to about 10% by weight of a polyethylene glycol having an average molecular weight of 1000 as the sole polyethylene glycol said $Sn^{2+}$ being stable, freely available, and not in chemical combination with other ingredients.

2. The composition of claim 1 wherein $SnF_2$ is present in the composition at a concentration of about 0.35 to about 0.5% by weight.

3. The composition of claim 1 wherein anhydrous glycerine is present in the composition at a concentration of about 90 to about 95% by weight.

4. The composition of claim 1 wherein the polyethylene glycol is present in the composition at a concentration of about 5.0 to about 8.0% by weight.

5. In a method for the treatment of dentine hypersensitivity by applying to the teeth a desensitizing amount of an oral composition in accordance with claim 1 containing $SnF_2$ and anhydrous glycerine, the improvement which comprises incorporating in the composition about 2.0 to about 10.0% by weight of a polyethylene glycol having an average molecular weight about 1000.

6. The method of claim 5 wherein the polyethylene glycol is present in the composition at a concentration of about 5.0 to about 8.0% by weight as the sole polyethylene glycol.

* * * * *